US012614250B2

(12) United States Patent
Eldar et al.

(10) Patent No.: US 12,614,250 B2
(45) Date of Patent: Apr. 28, 2026

(54) LEARNED SUPER RESOLUTION ULTRASOUND FOR IMPROVED BREAST LESION CHARACTERIZATION

(71) Applicant: Yeda Research And Development Co. Ltd, Rehovot (IL)

(72) Inventors: Yonina Eldar, Rehovot (IL); Or Bar-Shira, Tel Aviv (IL)

(73) Assignee: Yeda Research And Development Co. Ltd, Rehovot (IL)

( * ) Notice: Subject to any disclaimer, the term of this patent is extended or adjusted under 35 U.S.C. 154(b) by 0 days.

(21) Appl. No.: 18/561,314

(22) PCT Filed: May 18, 2022

(86) PCT No.: PCT/IB2022/054611
§ 371 (c)(1),
(2) Date: Nov. 16, 2023

(87) PCT Pub. No.: WO2022/243889
PCT Pub. Date: Nov. 24, 2022

(65) Prior Publication Data
US 2024/0249384 A1      Jul. 25, 2024

Related U.S. Application Data

(60) Provisional application No. 63/189,723, filed on May 18, 2021.

(51) Int. Cl.
*G06T 3/4053* (2024.01)
*A61B 8/00* (2006.01)
(Continued)

(52) U.S. Cl.
CPC .............. *G06T 3/4053* (2013.01); *A61B 8/13* (2013.01); *A61B 8/481* (2013.01); *A61B 8/5207* (2013.01); *A61B 8/5276* (2013.01); *G06T 3/4046* (2013.01)

(58) Field of Classification Search
CPC .......................................... G06T 3/4053–4076
See application file for complete search history.

(56) References Cited

U.S. PATENT DOCUMENTS

| | | | | |
|---|---|---|---|---|
| 2019/0365355 | A1* | 12/2019 | Eldar | A61B 8/488 |
| 2020/0126213 | A1* | 4/2020 | Wheaton | A61B 6/5205 |
| 2021/0407043 | A1* | 12/2021 | Jensen | G06T 5/70 |

FOREIGN PATENT DOCUMENTS

WO      2020252463 A1    12/2020

OTHER PUBLICATIONS

R. van Sloun et al, "Super-resolution Ultrasound Localization Microscopy through Deep Learning", arxiv.org, pp. 1-18, Apr. 2018 (Year: 2018).*

(Continued)

*Primary Examiner* — Nyrobi Celestine
(74) *Attorney, Agent, or Firm* — Heidi M. Brun

(57)          ABSTRACT
An ultrasound scanning system includes an ultrasound scanner, a trained spare recovery neural network and a super resolution image generator. The ultrasound scanner views a patient after intravenous injection of microbubbles and then generates a sequence of ultrasound images. The sequence of ultrasound images is formed of a sequence of B-mode ultrasound images and a sequence of contrast enhanced ultrasound images corresponding to the B-mode ultrasound images. The trained sparse recovery neural network is trained on synthesized images of point sources and generates, for at least one image of the sequence of contrast-enhanced ultrasound images, a super-resolved image of locations of the microbubbles in that image. The super resolution image generator receives an output of the trained sparse recovery neural network and generates therefrom a super-resolved image of a microvasculature through which the microbubbles flowed.

14 Claims, 8 Drawing Sheets

100

(51) Int. Cl.
     *A61B 8/13*        (2006.01)
     *G06T 3/4046*      (2024.01)

(56) References Cited

OTHER PUBLICATIONS

R. van Sloun et al, "Deep Learning for Super-resolution Vascular Ultrasound Imaging", ICASSP 2019-2019 IEEE International Conference on Acoustics, Speech and Signal Processing (ICASSP), pp. 1055-1059, Apr. 2019 (Year: 2019).*

O. Solomon et al, "Super-resolution Using Flow Estimation in Contrast Enhanced Ultrasound Imaging", CASSP 2019-2019 IEEE International Conference on Acoustics, Speech and Signal Processing (ICASSP), pp. 1338-1342, Apr. 2019 (Year: 2019).*

A. Bar-Zion et al, "Super-resolution ultrasound imaging of vascular structures with high temporal resolution", IEEE Transactions on Medical Imaging, pp. 1-11, Jan. 2016 (Year: 2016).*

J. Park et al., "Deep Learning-Based Super-resolution Ultrasound Speckle Tracking Velocimetry", Ultrasound in Medicine and Biology, vol. 46, No. 3, pp. 598-609, Dec. 2019 (Year: 2019).*

Q. Chen et al., "Current Development and Applications of Super-Resolution Ultrasound Imaging", Sensors, vol. 21, No. 2417, pp. 1-19, Feb. 2021 (Year: 2021).*

International Search Report for corresponding International Application PCT/IB2022/054611 mailed on Aug. 16, 2022.

Ruud J C Van Sloun et al: "Super-resolution ultrasound localization microscopy through deep learning", IEEE Transactions on Medical Imaging (2020).

Kirsten Christensen-Jeffries et al: "Super-resolution ultrasound imaging", Ultrasound in Medicine and Biology, vol. 46, No. 4, pp. 865-891, Jan. 21, 2020.

Saiprasad Ravishankar et al: "Image Reconstruction: From Sparsity to Data-adaptive Methods and Machine Learning", Arxiv.org, Cornell University Library, Apr. 5, 2019.

Matthieu Kowalski: "Thresholding RULES and iterative shrinking/thresholding algorithm: A convergence study", 2014 IEEE International Conference on Image Processing (ICIP), Oct. 27, 2014.

V. Monga, et al., "Algorithm Unrolling: Interpretable, Efficient Deep Learning for Signal and Image Processing", IEEE Signal Processing Magazine, vol. 38, issue 2, pp. 18-44, Mar. 2021.

A. Bar-Zion et al., "Sushi: Sparsity-based Ultrasound Super-Resolution Hemodynamic Imaging". IEEE transactions on Ultrasonics, Ferroelectrics, and Frequency Control 65(12), 2365-2380 (2018).

E. Betzig et al., "Imaging Intracellular Fluorescent Proteins at Nanometer Resolution". Science 313(5793), 1642-1645 (2006).

D. Cosgrove et al., "Imaging of Perfusion using Ultrasound". European Journal of Nuclear Medicine and Molecular Imaging 37(1), 65-85 (2010).

O. Couture et al., "Ultrafast Imaging of Ultrasound Contrast Agents". Ultrasound in Medicine & Biology 35(11), 1908--1916 (2009).

O. Couture et al., "Ultrasound Contrast Plane Wave Imaging". IEEE Transactions on Ultrasonics, Ferroelectrics, and Frequency Control 59(12), 2676-2683 (2012).

I. Daubechies et al., "An Iterative Thresholding Algorithm for Linear Inverse Problems with a Sparsity Constraint". Communications on Pure and Applied Mathematics: A Journal Issued by the Courant Institute of Mathematical Sciences 57(11), 1413-1457 (2004).

S. Dencks et al., "Clinical Pilot Application of Super-Resolution US Imaging in Breast Cancer". IEEE Transactions on Ultrasonics, Ferroelectrics, and Frequency Control 66(3), 517-526 (2018).

S.B. Fox et al., "Breast Tumour Angiogenesis". Breast Cancer Research 9(6), 1-11 (2007).

S. Gokhale: "Ultrasound Characterization of Breast Masses". The Indian Journal of Radiology & Imaging 19(3), 242 (2009).

A. Goussia et al., "Associations of Angiogenesis-related Proteins with Specific Prognostic Factors, Breast Cancer Subtypes and Survival Outcome in Early-stage Breast Cancer Patients". A Hellenic Cooperative Oncology Group (HECOG) Trial. Plos one 13(7), e0200302 (2018).

S. Harput et al., Two-Stage Motion Correction for Super-Resolution Ultrasound Imaging in Human Lower Limb. IEEE Transactions on Ultrasonics, Ferroelectrics, and Frequency Control 65(5), 803-814 (2018).

C. Huang et al., "Super-Resolution Ultrasound Localization Microscopy based on a High Frame-Rate Clinical Ultrasound Scanner: An In-Human Feasibility Study". arXiv preprint arXiv:2009.13477 (2020).

D. P. Kingma et al., "A Method for Stochastic Optimization". arXiv preprint arXiv:1412.6980 (2014).

T. Opacic et al., "Motion Model Ultrasound Localization Microscopy for Preclinical and Clinical Multiparametric Tumor Characterization". Nature Communications 9(1), 1-13 (2018).

M. J. Rust et al., Sub-Diffraction-Limit Imaging by Stochastic Optical Reconstruction Microscopy (STORM). Nature methods 3(10), 793-796 (2006).

Ruud J C Van Sloun et al., "Deep Learning in Ultrasound Imaging". Proceedings of the IEEE 108(1), 11-29 (2019).

O. Solomon et al., "Exploiting Flow Dynamics for Superresolution in Contrast-Enhanced Ultrasound". IEEE Transactions on Ultrasonics, Ferroelectrics, and Frequency Control 66(10), 1573-1586 (2019).

M. Toi et al., "Tumor Angiogenesis in Breast Cancer: Its Importance as a Prognostic Indicator and the Association with Vascular Endothelial Growth Factor Expression". Breast Cancer Research and Treatment 36(2), 193-204 (1995).

Ruud J C Van Sloun et al., Sparsity-Driven Super-Resolution in Clinical Contrast-Enhanced Ultrasound. In: 2017 IEEE International Ultrasonics Symposium (IUS). pp. 1-4. IEEE (2017).

* cited by examiner

LEARNED SUPER RESOLUTION ULTRASOUND FOR IMPROVED BREAST LESION CHARACTERIZATION

CROSS REFERENCE TO RELATED APPLICATIONS

This application is a National Phase of International Application No. PCT/IB2022/054611 having an international filing date of May 18, 2022, which in turn claims priority and benefit from U.S. provisional patent application 63/189,723, filed May 18, 2021, both of which are incorporated herein by reference.

FIELD OF THE INVENTION

The present invention relates generally to super-resolution of images and to super-resolution of ultrasound images in particular.

BACKGROUND OF THE INVENTION

Diagnostic imaging plays a critical role in healthcare, serving as a fundamental asset for timely diagnosis, disease staging, and management as well as for treatment choice, planning, guidance, and follow-up. As discussed in the article by Cosgrove, D., and Lassau, N. (Imaging of perfusion using ultrasound. European journal of nuclear medicine and molecular imaging 37(1), 65-85 (2010)), among the diagnostic imaging options, ultrasound imaging is uniquely positioned, being a highly cost-effective modality that offers the clinician and the radiologist an unmatched and invaluable level of interaction, enabled by its real-time nature and portability.

However, conventional ultrasound is limited in resolution by diffraction and thus cannot resolve the microvascular architecture.

Contrast-Enhanced US (CEUS), shown in FIG. 1 to which reference is now briefly made, is an improved type of ultrasound which uses ultrasound contrast agents (UCAs), formed of encapsulated gas microbubbles which are similar in size to red blood cells. As shown in FIG. 1, UCAs 10 are injected intravenously into the veins of a patient 12 and then a portion of patient 12, such as a breast (as shown), is scanned with an ultrasound probe 14. The ultrasound probe 14 generates raw ultrasound data which an ultrasound machine (not shown) processes either into standard ultrasound images (known as "B-mode ultrasound images") or, for CEUS systems, into "contrast-enhanced" ultrasound images 16 which show the contrast material of UCAs 10, making the vasculature through which the UCAs flow easier to view.

CEUS enables real-time hemodynamic and noninvasive perfusion measurements with high-penetration depth. However, the spatial resolution of conventional CEUS imaging is also bounded by diffraction.

Recently, the introduction of super-resolution Ultrasound Localization Microscopy (ULM) facilitates fine visualization and detailed assessment of capillary blood vessels. ULM relies on concepts borrowed from super-resolution fluorescence microscopy techniques, such as Photo-Activated Localization Microscopy (PALM) and Stochastic Optical Reconstruction Microscopy (STORM), which localize individual fluorescing molecules with subpixel precision over many images and sum all localizations to produce a super-resolved image. PALM and STORM are described in the following articles:

Rust, M. J., Bates, M., Zhuang, X.: Sub-diffraction-limit imaging by stochastic optical reconstruction microscopy (storm). Nature methods 3(10), 793-796 (2006); and Betzig, E., Patterson, G. H., Sougrat, R., Lindwasser, O. W., Olenych, S., Bonifacino, J. S., Davidson, M. W., Lippincott-Schwartz, J., Hess, H. F.: Imaging intracellular fluorescent proteins at nanometer resolution. Science 313(5793), 1642-1645 (2006).

The article by Van Sloun, R. J., Cohen, R., Eldar, Y. C. (Deep learning in ultrasound imaging. Proceedings of the IEEE 108(1), 11-29 (2019)) discusses a CEUS super-resolution method using raw data from research ultrasound scanners, taken at a high image rate.

SUMMARY OF THE PRESENT INVENTION

There is provided, in accordance with a preferred embodiment of the present invention, an ultrasound scanning system including an ultrasound scanner, a trained spare recovery neural network and a super resolution image generator. The ultrasound scanner views a human patient after intravenous injection of microbubbles and then generates a sequence of ultrasound images. The sequence of ultrasound images is formed of a sequence of B-mode ultrasound images and a sequence of contrast enhanced ultrasound images corresponding to the B-mode ultrasound images. The trained sparse recovery neural network is trained on synthesized images of point sources and generates, for at least one image of the sequence of contrast-enhanced ultrasound images, a super-resolved image of locations of the microbubbles in the at least one image. The super resolution image generator receives an output of the trained sparse recovery neural network and generates therefrom a super-resolved image of a microvasculature through which the microbubbles flowed.

Moreover, in accordance with a preferred embodiment of the present invention, the trained sparse recovery neural network includes multiple repeating blocks, wherein each block is a neural network version of a sparse recovery unit and has at least convolutional filters replacing matrix multiplication elements of the sparse recovery unit.

Further, in accordance with a preferred embodiment of the present invention, the sparse recovery unit implements an ISTA (iterative soft thresholding algorithm) and each block of the sparse recovery neural network includes a soft thresholding element replacing a soft thresholding operator of the ISTA.

Still further, in accordance with a preferred embodiment of the present invention, the system includes a pre-processor at least to reduce patient motion and tissue signals in the sequence of ultrasound images.

Moreover, in accordance with a preferred embodiment of the present invention, the sequence of ultrasound images has an image rate of 50 images/second or less.

Further, in accordance with a preferred embodiment of the present invention, the pre-processor includes a patient motion reducer to compute a cross-correlation of the B-mode ultrasound images across a pre-defined region of interest (ROI).

Still further, in accordance with a preferred embodiment of the present invention, the system includes a training system to provide synthesized example images to an untrained sparse recovery neural network.

Moreover, in accordance with a preferred embodiment of the present invention, the training system includes a high-resolution point source synthesizer to generate target images with a plurality of point sources therein on a high-resolution grid, and a low resolution convolver to convolve each target image at least with a selected one of a plurality of point spread functions to generate a low-resolution input image.

Further, in accordance with a preferred embodiment of the present invention, the microbubbles are used in contrast-enhanced ultrasound systems.

There is also provided, in accordance with a preferred embodiment of the present invention, an ultrasound scanning method which includes generating a sequence of ultrasound images when viewing a patient after intravenous injection of microbubbles, where the sequence of ultrasound images are formed of a sequence of B-mode ultrasound images and a sequence of contrast enhanced ultrasound images corresponding to the B-mode ultrasound images, using a trained sparse recovery neural network, trained on synthesized images of point sources, to generate, for at least one image of the sequence of contrast-enhanced ultrasound images, a super-resolved image of locations of the microbubbles in the at least one image, and generating a super-resolved image of a microvasculature through which the microbubbles flowed from an output of the trained sparse recovery neural network.

Moreover, in accordance with a preferred embodiment of the present invention, the method includes reducing patient motion and tissue signals in the sequence of ultrasound images. The reducing patient motion includes computing a cross-correlation of the B-mode ultrasound images across a pre-defined region of interest (ROI).

Further, in accordance with a preferred embodiment of the present invention, the method includes providing synthesized example images to an untrained sparse recovery neural network.

Still further, in accordance with a preferred embodiment of the present invention, the providing includes synthesizing target images with a plurality of point sources therein on a high-resolution grid and convolving each target image at least with a selected one of a plurality of point spread functions to generate a low-resolution input image.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
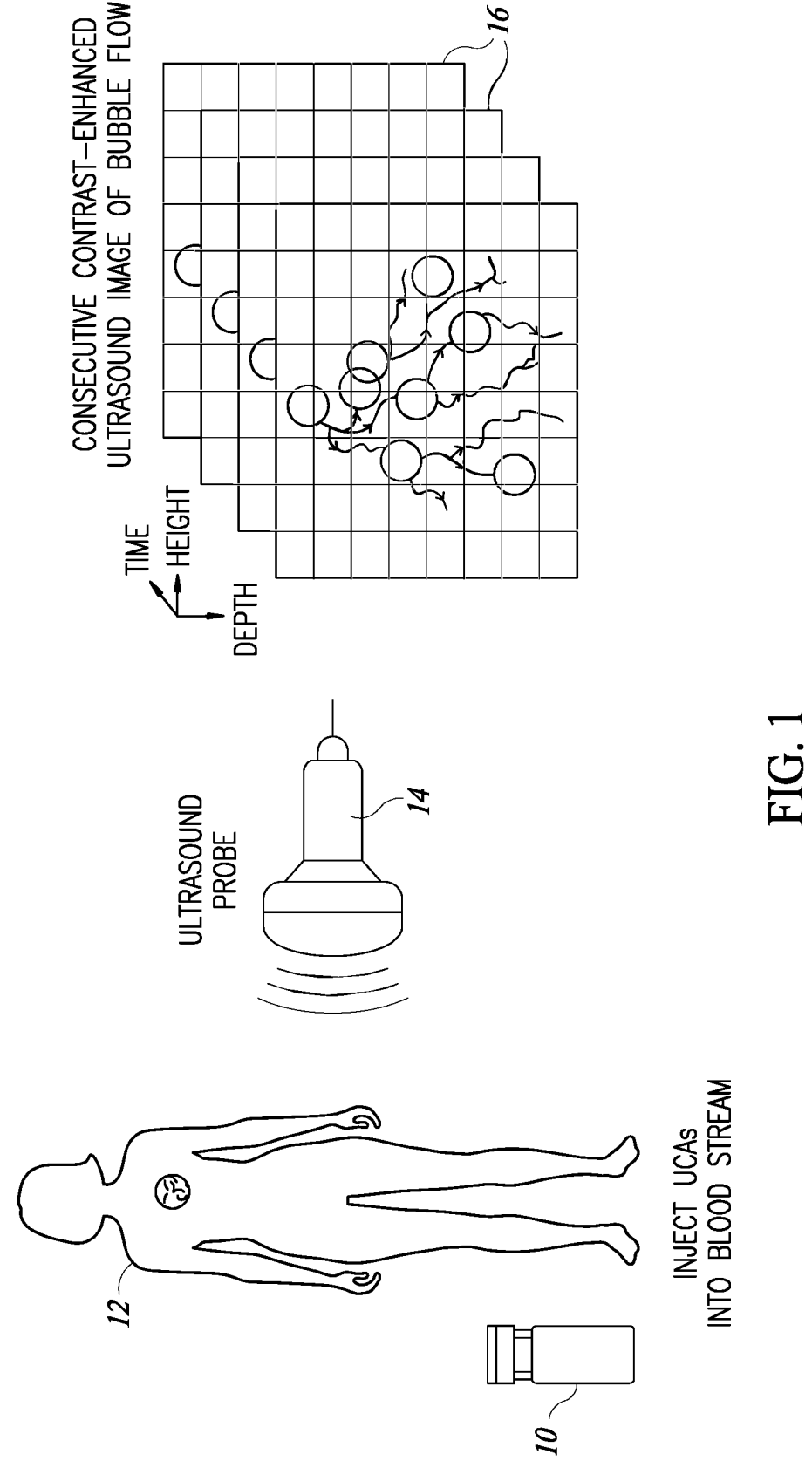
FIG. 1 is a schematic illustration of a Contrast-Enhanced US (CEUS) process.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Applicant has realized that the microbubbles used as ultrasound contrast agents (UCAs) in the prior art can be viewed as point emitters. If the concentration of point emitters is "sparse" in an ultrasound image, sparse recovery systems may be used to localize them (i.e., to determine their micrometric locations).

Since the microbubbles are purely intravascular, their localizations should yield a super-resolved map of the microvasculature. Super-resolved maps are discussed in the article by Christensen-Jeffries, K., et al., Super-resolution ultrasound imaging. Ultrasound in Medicine & Biology 46(4), 865-891 (2020). This may enable clinical ultrasound systems to image fine vessels with low flow velocities.

Figure 2:
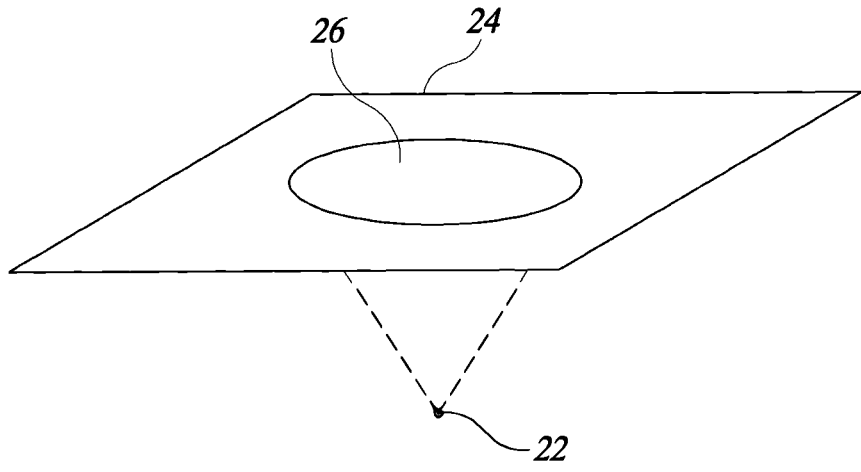
FIG. 2 is a schematic illustration of a single point emitter as viewed by a scanner.

Unfortunately, conventional ultrasound scanning systems are limited in resolution, which cause them to view the reflections of the microbubbles not as sharp points. This is shown in FIG. 2 to which reference is now briefly made. FIG. 2 shows a single point emitter 22 as viewed by a scanner 24, represented by an image plane. Scanner 24 sees a cloud 26 rather than the single point of point emitter 22. Cloud 26 defines the "point spread function" (PSF) of the scanning system (which includes the probe and the processing electronics) and the PSF defines by how much the entire scanning system "spreads" the signal from point emitter 22.

Figure 3:
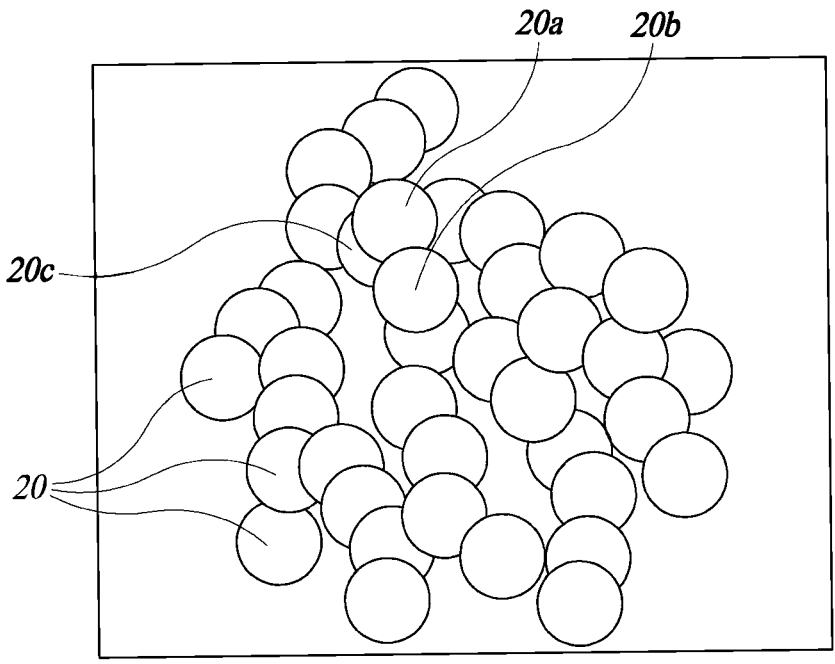
FIG. 3 is a schematic illustration of multiple round microbubbles as viewed by a scanner.

Thus, the system PSF may cause the scanning system to view the microbubbles as being overlapped. Moreover, they may be highly concentrated, which also makes it difficult for an ultrasound scanner to differentiate them. This is shown in FIG. 3, to which reference is now briefly made. The scanner's view of multiple round microbubbles 20 is shown. Many of the microbubbles, such as the ones labeled 20a, 20b and 20c, overlap each other, making it difficult to differentiate them.

Figure 4:
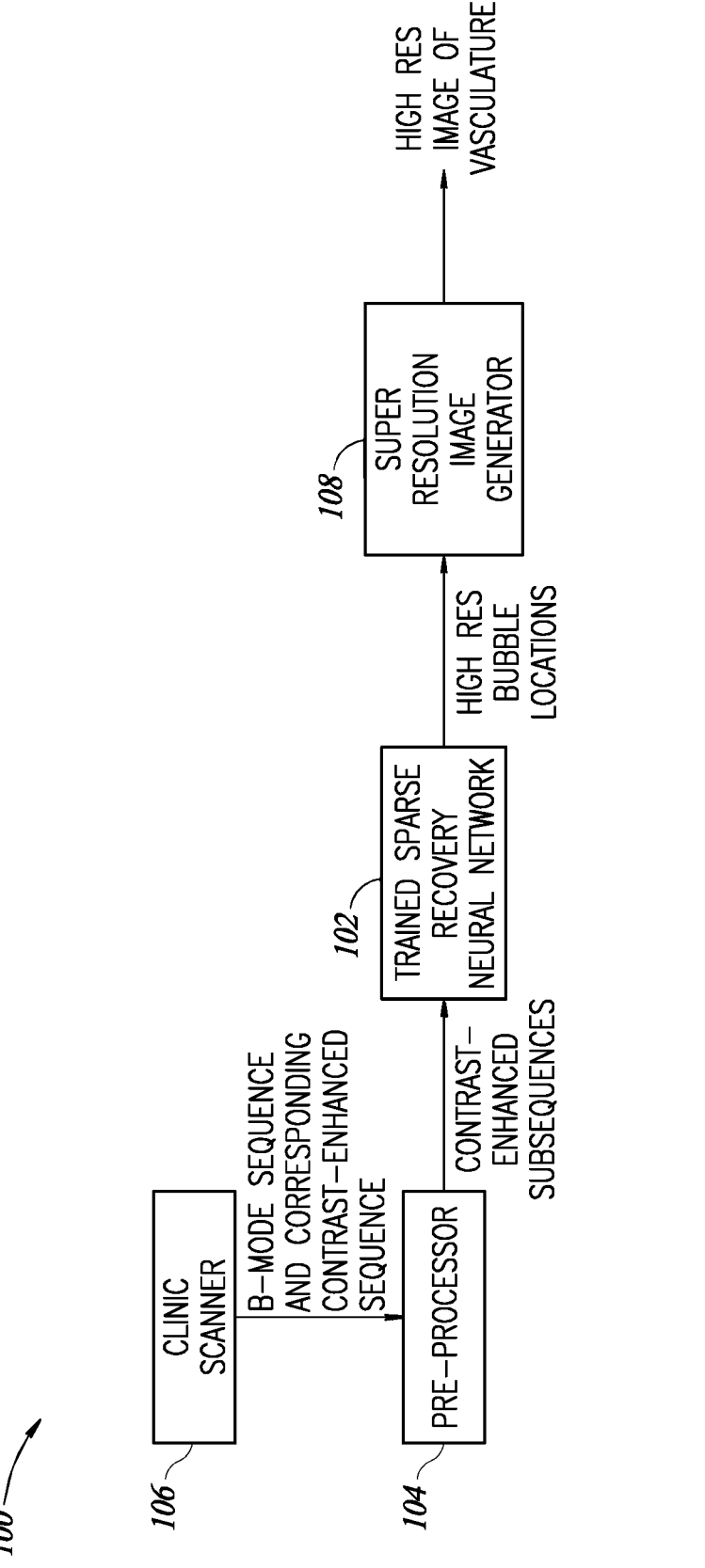
FIG. 4 is a block diagram illustration of a learned ultrasound super resolution system, constructed and operative in accordance with a preferred embodiment of the present invention.

Reference is now made to FIG. 4, which illustrates a learned ultrasound super resolution system 100, constructed and operative in accordance with a preferred embodiment of the present invention, which may provide super-resolution to ultrasound scans generated by a low-frame rate, clinical ultrasound scanner rather than a high frame rate, research ultrasound scanner. Learned super resolution system 100 comprises a trained sparse recovery neural network (SRNN) 102, a pre-processor 104, and a super resolution image generator 108.

A clinic scanner 106 may view an area of human patient 12 for an acquisition time of T seconds, where T may be long enough for microbubbles 12 to flow through the veins of patient 12 and typically is several minutes. Clinic scanner 106 may generate a sequence of ultrasound images, formed of a sequence of B-mode images as well as a corresponding sequence of contrast-enhanced images, at a low image rate of 15-50 images per second.

Pre-processor 104 may receive the sequence of ultrasound images from scanner 106 and may clean them up, using the B-mode sequence, to remove patient motion and to separate between signals from the microbubbles and signals from the tissues through which the ultrasound wave moved in the corresponding contrast-enhanced sequence.

Trained SRNN 102 may be based on any suitable neural network, such as a deep convolutional neural network, and may receive the contrast-enhanced images of the processed images. Trained SRNN 102 may determine the locations of microbubbles 20 on a high-resolution grid in each image of the received contrast-enhanced images, and super resolution image generator 108 may aggregate the locations from all the images, resulting in a high-resolution image of the vasculature.

Figure 5A:
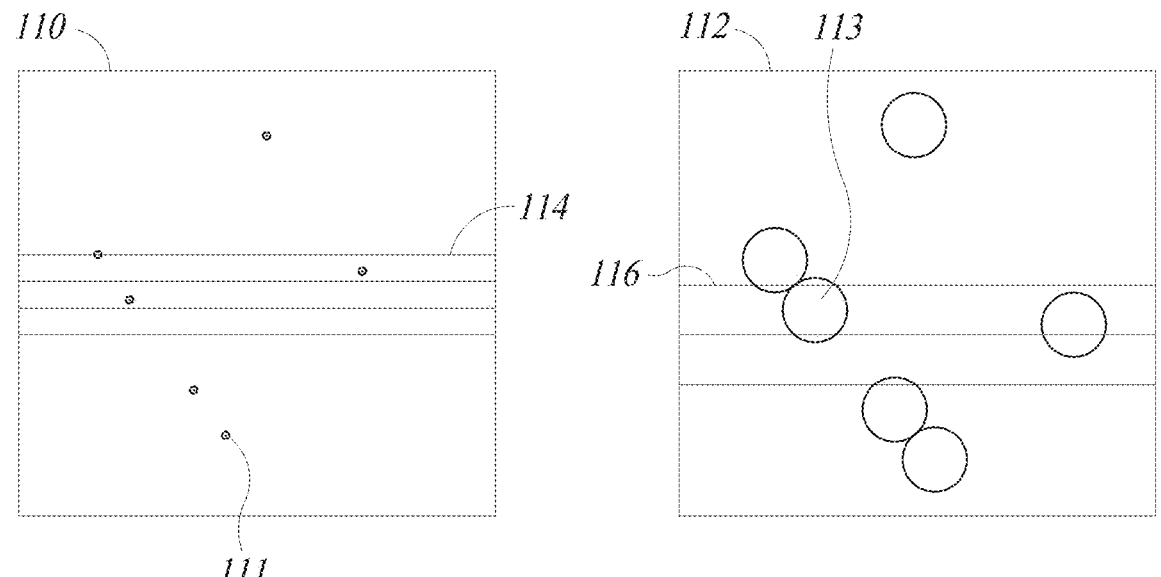
FIG. 5A is a schematic illustration of an example target image and the example input image 112 generated therefrom, useful in training the system of FIG. 4.

In accordance with a preferred embodiment of the present invention, SRNN 102 may be trained on a plurality of synthesized example input images. Reference is now made to FIG. 5A, which illustrates an example target (or 'truth') image 110 and the example input image 112 generated therefrom, useful in training SRNN 102.

Figure 5B:
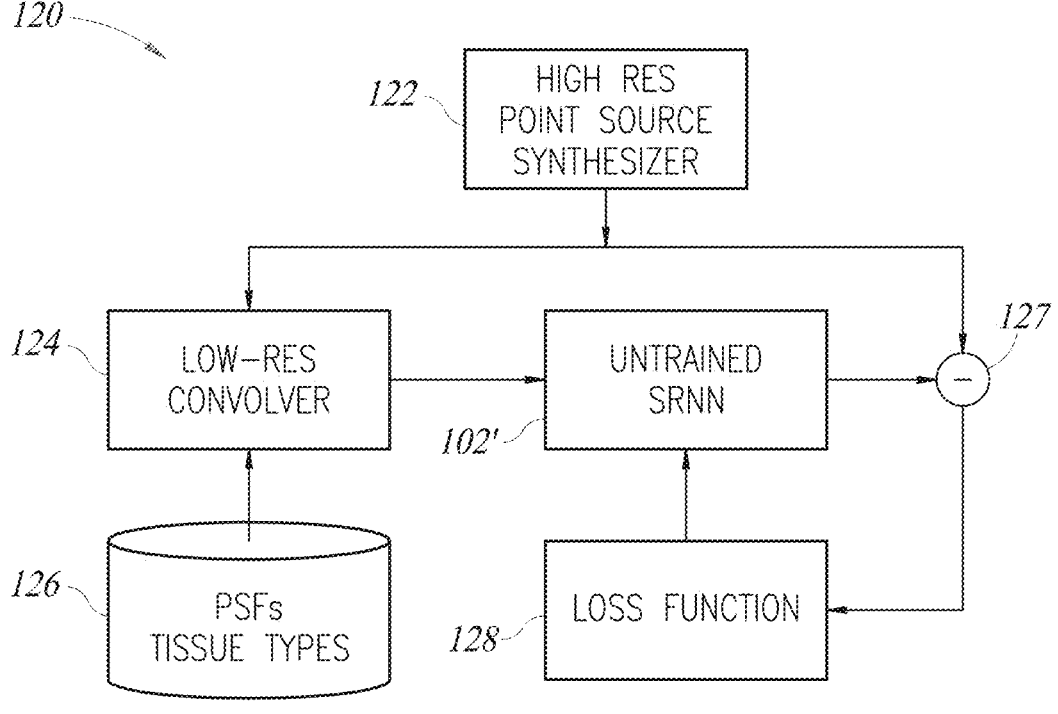
FIG. 5B is a schematic illustration of an exemplary training system for the system of FIG. 4.

Reference is also made to FIG. 5B, which illustrates an exemplary training system 120 for SRNN 102. Training system 120 may comprise a high-resolution point source synthesizer 122, and a low resolution convolver 124, operative to provide the synthesized example images to an untrained SRNN, here labeled 102'.

High resolution point source synthesizer 122 may generate a plurality of synthesized target images 110, each having a few point sources 111 (FIG. 5A) placed on a high-resolution image grid 114. For clarity, only a few horizontal lines in grid 114 are shown; it will be appreciated that grid 114 may have both vertical and horizontal lines throughout the image. Synthesizer 122 may randomly select the number of point sources and their locations within grid 114.

Low resolution convolver 124 may convolve each target image 110 with a different system PSF. For each target image 110, low resolution convolver 124 may place the resultant convolved clouds, labeled 113 in FIG. 5A, on a low-resolution image grid 116 (as for high resolution grid 114, only a few horizontal lines in low resolution grid 116 are shown), thereby generating an initial input image 112 associated with that target image 110. Low resolution convolver 124 may optionally add tissue texture, from one or more tissue types to each initial input image 112, thereby to generate each resultant, diffraction-limited, input image 112. Low resolution convolver 124 may associate the resultant input images 112 with the target images 110 from which they were generated.

It will be appreciated that tissue types may be defined by their density, location, intensities, and background noise, and that low resolution convolver 124 may randomly sample these, and the PSF parameters, from distributions that are defined at training. FIG. 5B shows these as being stored in a database 126, though this may not be necessary in all implementations.

Training system 120 may train untrained SRNN 102' via supervised learning on the target/input image pairs 110/112. Thus, the output of untrained SRNN 102' in response to each input image 112 may be compared to its associated target image 110 and used to correct SRNN 102' accordingly. Thus, training system 120 may achieve robust inference under a wide variety of synthesized imaging conditions.

Specifically, training system 120 may comprise a difference generator 127 to generate a difference image between each target image 110 and the output of untrained SRNN 102' in response to its associated input image 112. Training system 120 may calculate a loss function 128 from the difference. As is known in neural networks, loss function 128 may be utilized to update untrained SRNN 102', to improve its response. Training system 120 may iterate multiple times before untrained SRNN 102' may become trained SRNN 102, able to locate microbubbles 20 from data of clinical ultrasound systems.

In one exemplary training system 120, untrained SRNN 102' may be trained through loss minimization, such as with a back propagation algorithm, such as the ADAM optimizer. An exemplary loss function may be:

$$L(X, Y|\theta) = \|f(X|\theta) - G * Y\|_2^2 + \lambda \|f(X|\theta)\|_1^1$$

where Y is the target image containing the true microbubble locations, X is the low-resolution input, and f (X|θ) is the network output. A (which may be set to a value between 0 and 1) is a regularization parameter that promotes sparsity of the recovered image, and G is a known Gaussian filter (standard deviation can be set to 1 pixel). The use of G may enable the network to be more forgiving to small errors in the localization and promote convergence of the network.

It will be appreciated that other metrics and other synthesized examples may be used for training system 120. Any suitable training system 120 which may generate exemplary images having multiple, variable parameters which affect the quality of the ultrasound images may be utilized.

Figures 6A, 6B:
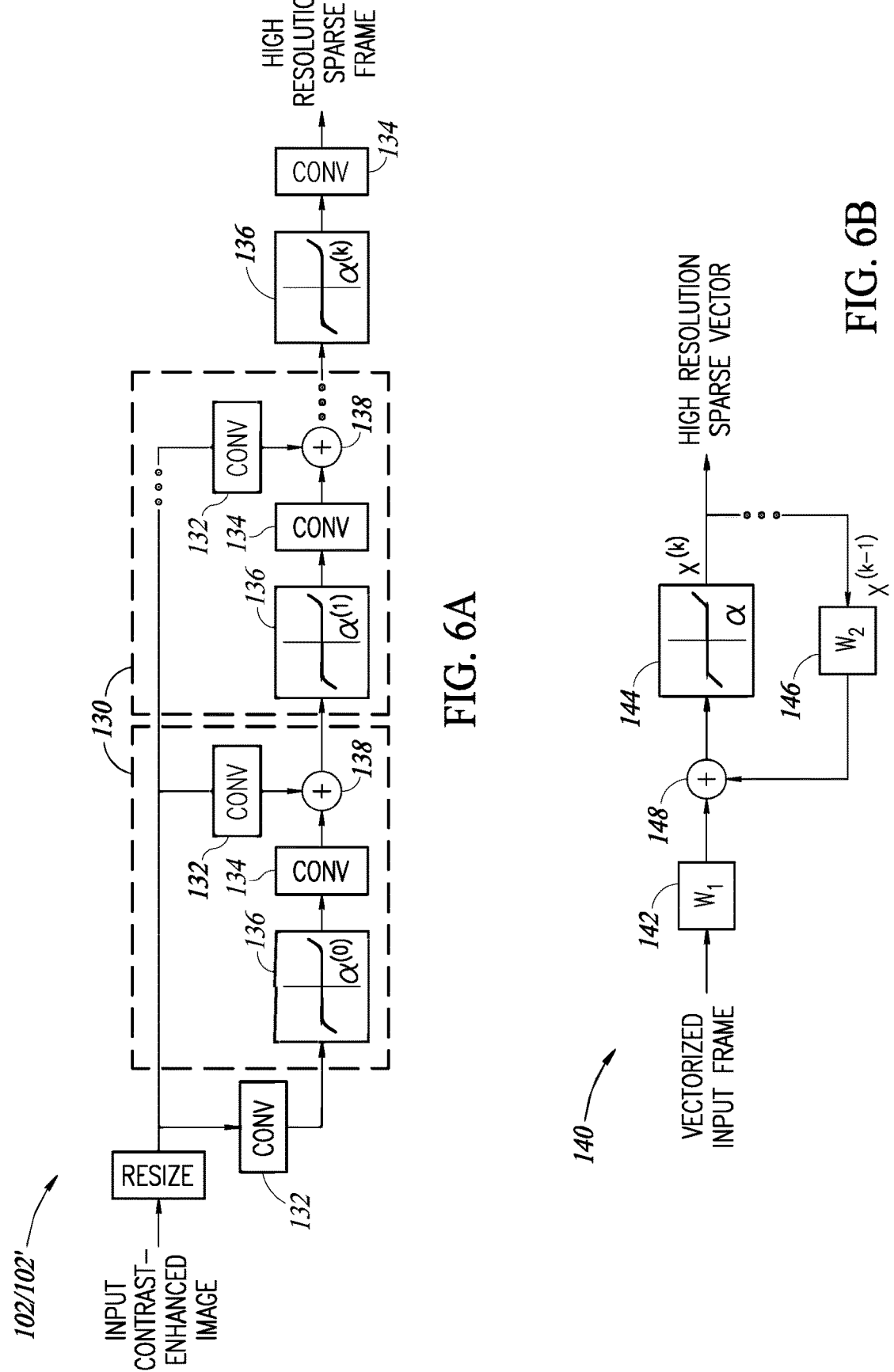
FIG. 6A is a schematic illustration of a sparse recovery neural network (SRNN) built of multiple repeating blocks.
FIG. 6B is a schematic illustration of an exemplary ISTA unit used to build the SRNN of FIG. 6A.

As shown in FIG. 6A, to which reference is now made, SRNN 102 may be built of multiple repeating blocks 130, where each block 130 may be a neural network version of a sparse recovery system. Any suitable sparse recovery system may be utilized to generate blocks 130, as described in detail hereinbelow. Building SRNN 102 in this way may provide it with an interpretable artificial intelligence framework, as discussed in the article by V. Monga, et al. ("Algorithm Unrolling: Interpretable, Efficient Deep Learning for Signal and Image Processing", IEEE Signal Processing Magazine, vol. 38, issue 2, pp. 18-44, March 2021).

In one example, each block 130 may be an unrolled version of the sparse recovery system and, in one further example, the sparse recovery system may be one implementing ISTA (iterative soft thresholding algorithm). ISTA has been shown to make effective use of sparsity to find the locations of ultrasound contrast agents (UCAs).

FIG. 6B, to which reference is now made, illustrates an exemplary ISTA unit 140 comprising two multipliers 142 and 146, a soft thresholding operator 144 and an adder 148. The input to ISTA is a vector version of the ultrasound image. Multiplier 142 transforms each input vector with a function of a matrix H related to the point spread function (PSF) of the ultrasound scanner. For example, the function may be $\mu H^T$, where matrix H and u are user defined.

Adder 148 adds a remnant signal to the output of multiplier 142 and then soft thresholding operator 144 thresholds the remnant signal, using a soft thresholding operation defined by a user-defined soft thresholding operator a. The output of operator 144 is fed back, via multiplier 146, to generate the remnant signal. For example, multiplier 146 may implement matrix multiplication of $1-\mu H^T H$.

ISTA unit 140 typically converges after N iterations and produces a high-resolution vector of microbubble locations.

Returning to FIG. 6A, each SRNN block 130 may have convolutional filters 132 and 134 replacing multipliers 142 and 146, respectively, of ISTA system 140, as well as a soft thresholding element 136 replacing soft threshold operator 144, and an adder 138 replacing adder 148. The parameters of convolutional filters 132 and 134 and of soft thresholding element 136 may be learned during training.

Exemplary SRNN 102 of FIG. 6A has three blocks 130, where two blocks are complete and the third one is divided, having a convolutional filter 132 before the other blocks 130 and having soft thresholding element 136 and convolutional filter 134 after the other blocks 130.

Since each SRNN block 130 may emulate ISTA unit 140, SRNN 102 may inherit the prior structures and domain knowledge of ISTA unit 140, rather than learn them from intensive training data. This may enable trained SRNN 102 to generalize from synthesized data.

It will be appreciated that SRNN 102 may adapt to the data such that the specifics of the ultrasound scanning system do not need to be known.

Figure 7:
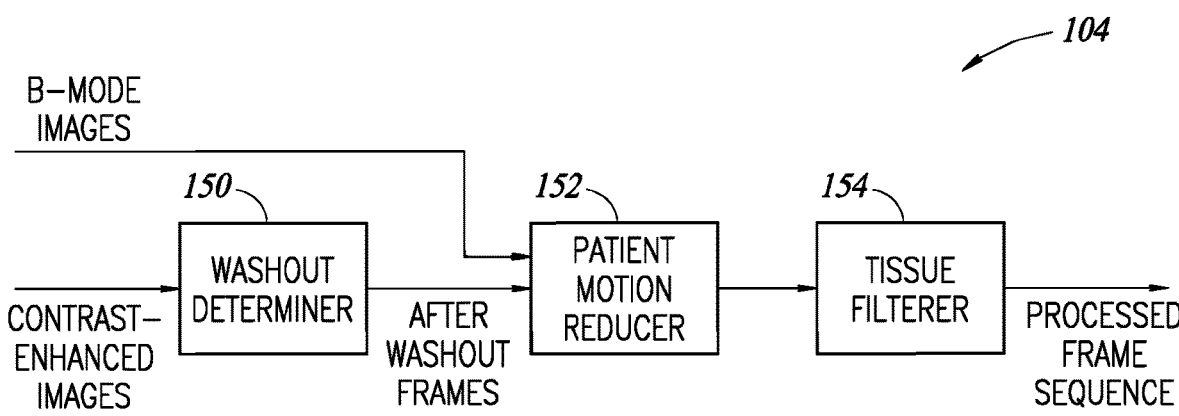
FIG. 7 is a schematic illustration of an exemplary pre-processor.

Reference is now made to FIG. 7, which illustrates the elements of an exemplary pre-processor 104, which may clean up images in the clinic scans to remove patient motion and to separate the microbubble signal from the tissue signal. It will be appreciated that any suitable pre-processor which may receive a sequence of ultrasound images from clinic ultrasound scanner 14, generated when viewing an area of patient 12 during acquisition time T, may be utilized.

It will be appreciated that the total number of detected vessels within acquisition time T is influenced by the flow-rate of microbubbles in the vessels which, in turn, depends on the blood flow in the vessels and on the concentration of the microbubbles in the blood, as discussed in the article by Dencks, S., et al (Clinical pilot application of super-resolution us imaging in breast cancer. IEEE transactions on ultrasonics, ferroelectrics, and frequency control 66(3), 517-526 (2018)). Therefore, pre-processor 104 may initially determine when the microbubbles are in the washout phase (i.e., when there is a maximum concentration of microbubbles) such that a large number of blood vessels can be detected. To this end, pre-processor 104 comprises a washout determiner 150 to find a maximum of a time intensity curve (TIC), calculated as the mean intensity at each contrast-enhanced ultrasound image. Washout determiner 150 may provide a subsequence comprising those of the ultrasound images which came after the maximum intensity was reached.

Pre-processor 104 may also comprise a patient motion reducer 152 and a tissue filterer 154. Patient motion reducer 152 may find subsequences within the output of washout determiner 150 which have similar images. Since microbubbles 20 are not visible in the B-mode images (though they are visible in the corresponding contrast-enhanced images), patient motion reducer 152 may operate on the B-mode images without disturbing the location estimation of microbubbles 10 that SRNN 102 may perform.

Motion reducer 152 may compute a cross-correlation of the B-mode ultrasound images across a pre-defined region of interest (ROI) having sufficient contrast. Motion reducer 152 may assign consecutive images to the same subsequence if their cross-correlation is above a predefined percentage, such as over 80%, and may select subsequences containing more than 1000 images.

Motion reducer 152 may then correct for small motions in the selected subsequences using image registration that accounts for translation. Motion reducer 152 may use a transformation matrix on the B-mode images, where, for example, the first image of a sequence may be the reference image for all later transformations. Other images may serve as reference images, as desired.

Tissue filterer 154 may be any suitable filterer which may reduce signals from tissues. For example, tissue filterer 154 may apply a spatiotemporal singular-value-decomposition (SVD)-based filter to the selected contrast-enhanced subsequences generated by motion reducer 152 to remove the tissue information from the images in the selected subsequences, generally leaving moving microbubble information in the images of the selected subsequences. These pre-processed images may then be provided to trained SRNN 102, which may generate super-resolved image images therefrom.

Figure 8:
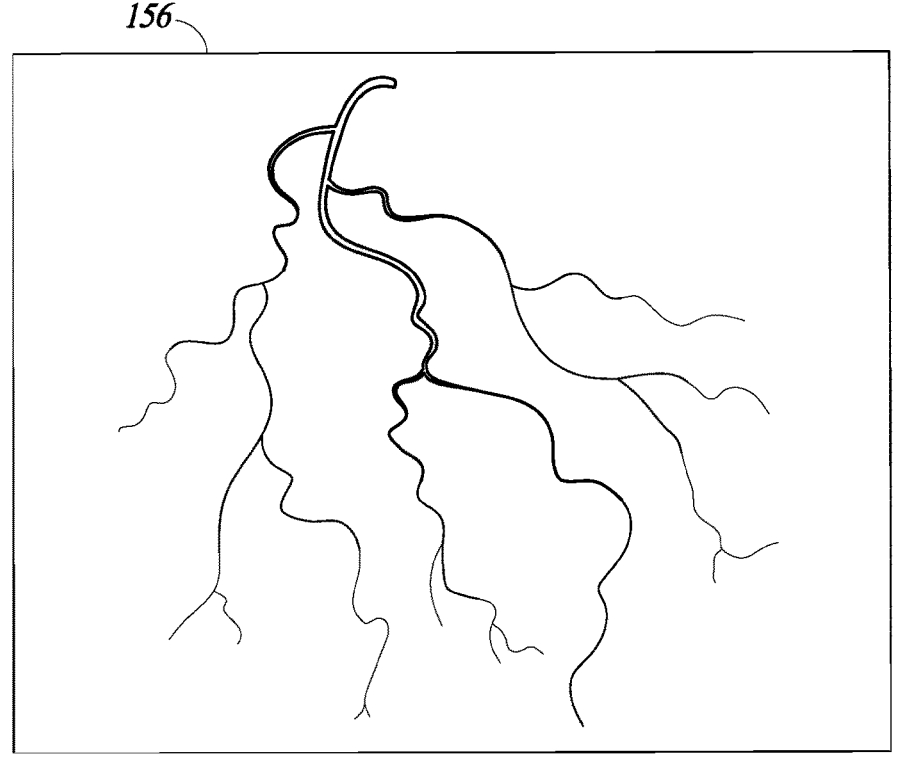
FIG. 8 is a schematic illustration of an exemplary super-resolved image.

Super resolution image generator 104 may receive the super-resolved image images, which have the locations of the microbubbles throughout the subsequence, and may aggregate the images, such as by summing, finding those with a maximum value, etc. Optionally, the summed result may be post-filtered. The result is a super-resolved image 156 of the microvasculature. FIG. 8, to which reference is now briefly made, shows one exemplary super-resolved image 156 showing a simplified version of the microvasculature through which microbubbles 20 flowed.

Figure 9:
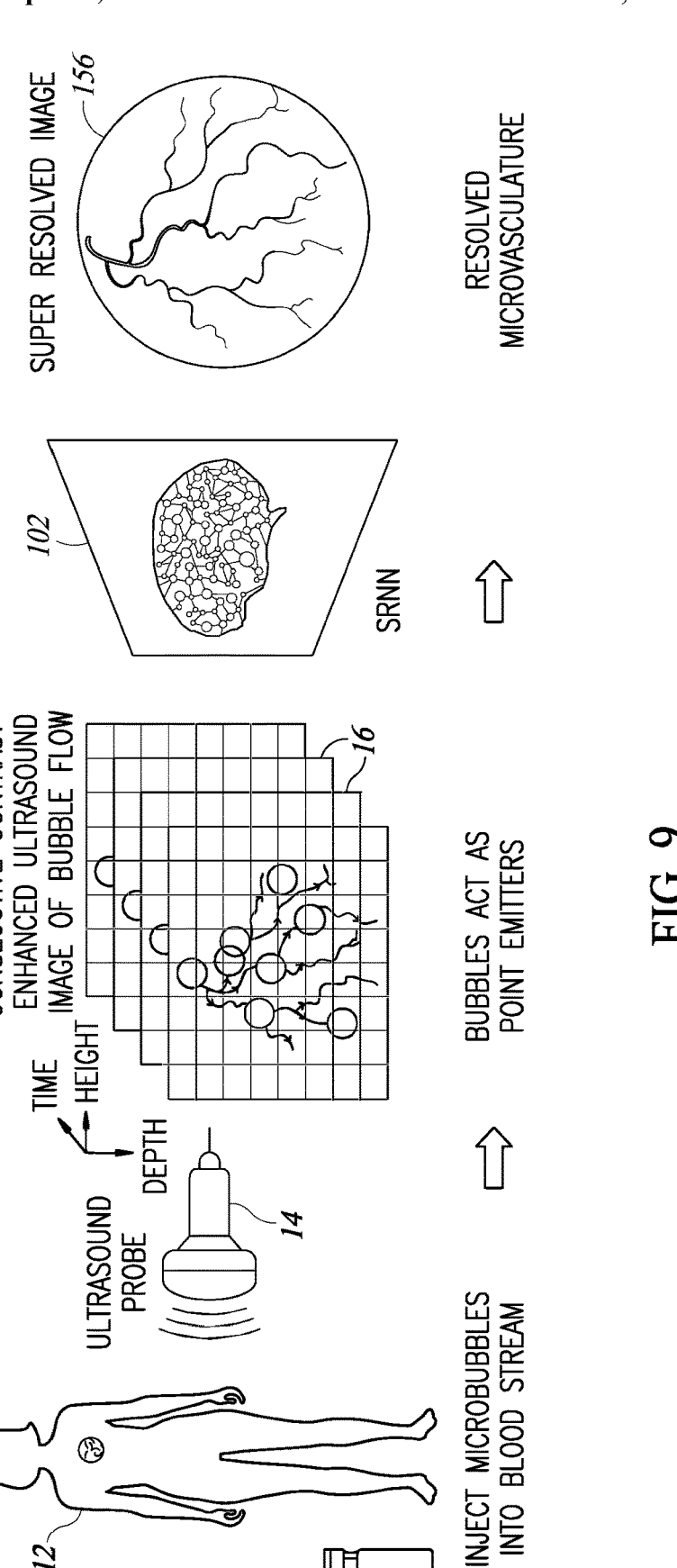
FIG. 9 is a schematic illustration of a learned ultrasound super resolution system in operation.

Reference is now made to FIG. 9, which illustrates learned ultrasound super resolution system 100 in operation, using trained SRNN 102. Initially, the clinician may inject microbubbles 20 into bloodstream of patient 12. The clinician may scan patient 12 with clinical ultrasound scanner 14 to receive both consecutive B-mode ultrasound images (not shown) and contrast-enhanced images 16. Pre-processor 104 may process the sequence of ultrasound images (both B-mode and contrast-enhanced) to remove patient motion and to separate the microbubble signal from the tissue signal. Trained SRNN 102 may operate on each contrast-enhanced image of the processed sequence and, for each image, may output the microbubble locations in that image on a high-resolution grid. Thus, the output of trained SRNN 102 may be a sequence of high-resolution microbubble images (i.e., super-resolved images) which super resolution image generator 108 may utilize to generate a single super-resolved image 156.

It will be appreciated that learned ultrasound super resolution system 100 may bring value to a wide range of clinical applications. For example, it may improve characterization of lesions found in breast cancers by enabling visualization of the dynamic vascular pattern in a lesion with respect to its surrounding tissue.

Figure 10:
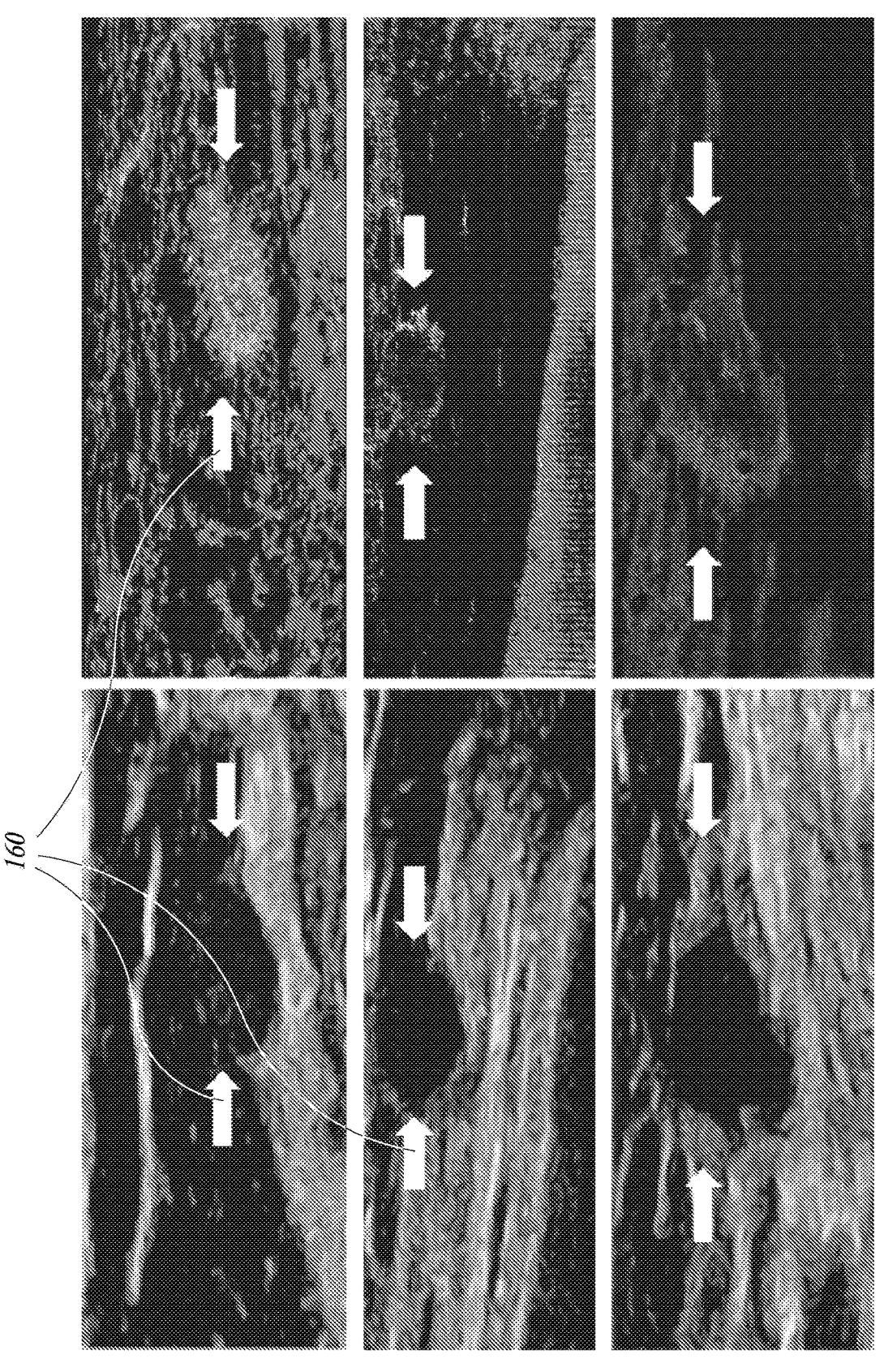
FIG. 10 are super resolved scans of three different types of lesions.

Reference is now briefly made to FIG. 10, which are super resolved scans of three different types of lesions in breasts of three patients. The images on the left are the B-mode ultrasound images and the images on the right are the super resolution recoveries. The arrows 160 point to the lesions. Note that the three lesions look very similar in the B-mode images, being circular black areas.

The two top figures, labeled A, show a benign fibroadenoma. The super resolution recovery shows an oval, well circumscribed mass with homogeneous high vascularization. The two middle figures, labeled B, show a benign cyst. The super resolution recovery shows a round structure with a high concentration of blood vessels at the periphery of the lesion. The two bottom figures, labeled C, show an invasive ductal carcinoma, which is malignant. The super resolution recovery shows an irregular mass with ill-defined margins, a high concentration of blood vessels at the periphery of the mass, and a low concentration of blood vessels at the center of the mass.

Thus, the super resolution recoveries generated by learned ultrasound super resolution system 100 may enable differentiation of different types of breast cancer lesions using standard B-mode and contrast-enhanced images from clinical scans. System 100 may be useful in differentiating the different types of lesions, tumors, growths, etc.

It will be appreciated that learned ultrasound super resolution system 100 may also be useful for diagnosis and monitoring of inflammatory diseases which are associated with hyperemia (i.e., an increased blood flow) to the inflamed tissue. One such inflammatory disease is Inflammatory Bowel Disease.

Learned ultrasound super resolution system 100 may also be useful for diagnosis and monitoring of medical pathologies in which microvascular networks play an important role, such as vasa vasorum and intraplaque neovascularization in atherosclerosis.

It will be appreciated that learned ultrasound super resolution system 100 may increase the effectiveness of clinical US scanners by adding an interpretable artificial intelligence framework. As a result, learned ultrasound super resolution system 100 may enhance the treatment capabilities of vasculature effected pathologies. It may improve the ability of clinical ultrasound scanners to differentiate between inflammatory and fibrotic phases of disease, which may affect treatment choices.

Unless specifically stated otherwise, as apparent from the preceding discussions, it is appreciated that, throughout the specification, discussions utilizing terms such as "processing," "computing," "calculating," "determining," or the like, refer to the action and/or processes of a general purpose computer of any type, such as a client/server system, mobile computing devices, smart appliances, cloud computing units or similar electronic computing devices that manipulate and/or transform data within the computing system's registers and/or memories into other data within the computing system's memories, registers or other such information storage, transmission or display devices.

Embodiments of the present invention may include apparatus for performing the operations herein. This apparatus may be specially constructed for the desired purposes, or it may comprise a computing device or system typically having at least one processor and at least one memory, selectively activated or reconfigured by a computer program stored in the computer. The resultant apparatus when instructed by software may turn the general-purpose computer into inventive elements as discussed herein. The instructions may define the inventive device in operation with the computer platform for which it is desired. Such a computer program may be stored in a computer readable storage medium, such as, but not limited to, any type of disk, including optical disks, magnetic-optical disks, read-only memories (ROMs), volatile and non-volatile memories, random access memories (RAMs), electrically programmable read-only memories (EPROMs), electrically erasable and programmable read only memories (EEPROMs), magnetic or optical cards, Flash memory, disk-on-key or any other type of media suitable for storing electronic instructions and capable of being coupled to a computer system bus. The computer readable storage medium may also be implemented in cloud storage.

Some general-purpose computers may comprise at least one communication element to enable communication with a data network and/or a mobile communications network.

The processes and displays presented herein are not inherently related to any particular computer or other apparatus. Various general-purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the invention as described herein.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An ultrasound scanning system comprising:

an ultrasound scanner viewing a human patient after intravenous injection of microbubbles, said ultrasound scanner to generate a sequence of ultrasound images, wherein said sequence of ultrasound images is a sequence of B-mode ultrasound images and a sequence of contrast enhanced ultrasound images corresponding to said B-mode ultrasound images;

a training system to provide synthesized images to an untrained sparse recovery neural network, said training system comprising:

a high-resolution point source synthesizer to generate synthesized target images with a plurality of randomly selected point sources therein on a high-resolution grid, wherein both a number of said point sources and locations of said point sources on said high-resolution grid are randomly selected to generate each of said synthesized target images; and a low resolution convolver to convolve each said target image at least with a selected one of a plurality of different point spread functions to generate an associated synthesized low-resolution input image;

a trained sparse recovery neural network, trained on said synthesized target images and said associated synthesized low-resolution input images, to generate, in response to at least one image of said sequence of contrast-enhanced ultrasound images, a super-resolved microbubbles image of locations of said microbubbles in said at least one image; and a super resolution image generator to receive said super-resolved microbubbles image and to generate therefrom a super-resolved microvasculature image of a microvasculature through which said microbubbles flowed.

2. The system of claim 1, wherein said trained sparse recovery neural network comprises multiple repeating blocks, wherein each block is a neural network version of an ISTA (iterative soft thresholding algorithm) comprising convolutional filters and a soft thresholding element.

3. The system of claim 1 further comprising a pre-processor at least to reduce patient motion and tissue signals in said sequence of ultrasound images.

4. The system of claim 1 wherein said sequence of ultrasound images has an image rate of 50 images/second or less.

5. The system of claim 3 wherein said pre-processor comprises a patient motion reducer to compute a cross-correlation of said B-mode ultrasound images across a pre-defined region of interest (ROI) and to correct for small motions in subsequences of images whose cross-correlation is above a predefined percentage.

6. The system of claim 1, wherein said ultrasound scanner is a contrast-enhanced ultrasound scanner using said microbubbles.

7. An ultrasound scanning method comprising:

generating a sequence of ultrasound images when viewing a human patient after intravenous injection of microbubbles, wherein said sequence of ultrasound images is a sequence of B-mode ultrasound images and a sequence of contrast enhanced ultrasound images corresponding to said B-mode ultrasound images;

providing synthesized example images to an untrained sparse recovery neural network, said providing comprising:

synthesizing target images with a plurality of randomly selected point sources therein on a high-resolution grid, wherein said synthesizing comprises randomly selecting both a number of said point sources and locations of said point sources on said high-resolution grid; and convolving each said target image at least with a selected one of a plurality of different point spread functions to generate an associated synthesized low-resolution input image;

using a trained sparse recovery neural network, trained on said synthesized target images and said associated synthesized low-resolution input images, to generate, in response to at least one image of said sequence of contrast-enhanced ultrasound images, a super-resolved microbubbles image of locations of said microbubbles in said at least one image; and generating a super-resolved microvasculature image of a microvasculature through which said microbubbles flowed from said super-resolved microbubbles image.

8. The method of claim 7, wherein said trained sparse recovery neural network comprises multiple repeating blocks, wherein each block is a neural network version of an ISTA (iterative soft thresholding algorithm) comprising convolutional filters and a soft thresholding element.

9. The method of claim 7 further comprising reducing patient motion and tissue signals in said sequence of ultrasound images.

10. The method of claim 7 wherein said sequence of ultrasound images has an image rate of 50 images/second or less.

11. The method of claim 9, wherein said reducing patient motion comprising computing a cross-correlation of said B-mode ultrasound images across a pre-defined region of interest (ROI) and correcting for small motions in subsequences of images whose cross-correlation is above a pre-defined cross-correlation percentage.

12. The method of claim 7, wherein said microbubbles are used in a contrast-enhanced ultrasound scanner.

13. The system of claim 1, wherein said low resolution convolver is configured to:

produce convolved images by convolving each said target image with said selected one of a plurality of different point spread functions; and add tissue texture from one or more tissue types to each said convolved image to generate said associated synthesized low-resolution input image.

14. The method of claim 7, wherein said step of generating an associated synthesized low-resolution input image comprises:

producing convolved images by convolving each said target image with said selected one of a plurality of different point spread functions; and adding tissue texture from one or more tissue types to each said convolved image to generate said associated synthesized low-resolution input image.

* * * * *